(12) United States Patent
Oti et al.

(10) Patent No.: US 8,197,486 B2
(45) Date of Patent: Jun. 12, 2012

(54) SURGICAL CUTTING GUIDE

(75) Inventors: James A. Oti, Franklin, MA (US); Kyle S. Moore, Acushnet, MA (US)

(73) Assignee: DePuy Products, Inc., Warsaw, IN (US)

( * ) Notice: Subject to any disclaimer, the term of this patent is extended or adjusted under 35 U.S.C. 154(b) by 1238 days.

(21) Appl. No.: 11/903,102

(22) Filed: Sep. 20, 2007

(65) Prior Publication Data

US 2009/0082774 A1 Mar. 26, 2009

(51) Int. Cl.
*A61F 5/00* (2006.01)
(52) U.S. Cl. .......................................... 606/87
(58) Field of Classification Search .............. 606/87–89; 144/144.1, 144.51, 145.1; 33/626, 628, 630, 33/633, 640
See application file for complete search history.

(56) References Cited

U.S. PATENT DOCUMENTS

| | | | |
|---|---|---|---|
| 4,926,847 A * | 5/1990 | Luckman | 606/88 |
| 4,979,949 A | 12/1990 | Matsen, III et al. | |
| 5,624,444 A | 4/1997 | Wixon et al. | |
| 5,749,876 A | 5/1998 | Duvillier et al. | |
| 5,897,559 A | 4/1999 | Masini | |
| 5,944,722 A | 8/1999 | Masini | |
| 6,007,537 A | 12/1999 | Burkinshaw et al. | |
| 6,440,140 B2 | 8/2002 | Bullivant et al. | |
| 6,558,391 B2 | 5/2003 | Axelson, Jr. et al. | |
| 6,770,077 B2 | 8/2004 | Van Zile et al. | |
| 6,852,115 B2 | 2/2005 | Kinnett | |
| 7,104,996 B2 | 9/2006 | Bonutti | |
| 7,172,596 B2 | 2/2007 | Coon et al. | |
| 7,621,919 B2 * | 11/2009 | Williams et al. | 606/87 |
| 2006/0111725 A1 | 5/2006 | Biegun | |

FOREIGN PATENT DOCUMENTS

| | | |
|---|---|---|
| DE | 202006014895 | 11/2006 |
| WO | 2005084558 | 9/2005 |
| WO | 2005110249 | 11/2005 |

OTHER PUBLICATIONS

European search report in a corresponding European application (i.e. EP 08 16 4570) is also enclosed that identifies the seven (7) references cited in this Supplemental Information Disclosure Statement (3 pages).

* cited by examiner

*Primary Examiner* — Anu Ramana
(74) *Attorney, Agent, or Firm* — Maginot, Moore & Beck

(57) ABSTRACT

A surgical cutting guide is adapted to receive a cutting instrument during a surgical procedure. The surgical cutting guide comprises at least one body portion including a bone engaging surface. A plurality of separate plates are secured to the at least one body portion. At least one cutting slot is formed in the surgical cutting guide between the plurality of separate plates. The at least one cutting slot is configured to receive the cutting instrument and orient the cutting instrument for the surgical procedure. The at least one body portion is comprised of a first material, such as a plastic material, and the plurality of separate plates are comprised of a second material, such as a metal material.

11 Claims, 7 Drawing Sheets

SURGICAL CUTTING GUIDE

FIELD

This invention relates to the field of orthopedics, and more particularly to instruments that are secured to the bone during orthopedic surgery.

BACKGROUND

Many orthopedic procedures involve tools or other instruments that assist the surgeon during the surgery. One such instrument is the cutting guide which is used during orthopedic surgery to assist the surgeon in making proper bone cuts. Cutting guides are typically provided in the form of blocks that include slots or other guides that show the surgeon where the bone is to be cut.

Cutting guides are generally formed from a single block of material comprised of stainless steel and/or titanium or other materials used in the art. When forming the cutting guide, the block of stainless steel/titanium material is cut or otherwise shaped to provide the desired slots and other features for the block. Accordingly, cutting blocks may be formed using EDM (electrical discharge machining) procedures, milling procedures, grinding procedures, blasting procedures, as well as other procedures as will be recognized by those in the art. The cutting and grinding involved with these procedures results in scrap product that typically goes to waste following the manufacture of the cutting block.

The stainless steel/titanium material used to form cutting blocks is becoming increasingly expensive and difficult to procure. This adds a substantial cost to the process used to form the material. In addition, the orthopedic instrument market continues to evolve, and instrument designs and configurations are becoming increasingly complex. It is often difficult and expensive to produce these more complex designs using traditional cutting and grinding procedures. Furthermore, the solid stainless steel and titanium cutting blocks tend to be rather heavy, contributing to the overall weight of a surgical instrument set and tray that must be handled by operating room personnel.

In view of the foregoing, it would be advantageous to provide a cutting guide that is less expensive to produce than previous cutting guides. It would also be advantageous if the manufacture of such a cutting guide resulted in less scrap. In addition, it would be advantageous if such a cutting guide could have a relatively complex design and still be manufactured with relative ease. Furthermore, it would be advantageous if such a cutting guide had a relatively light weight.

While it would be desirable to provide a cutting guide that includes one or more of the foregoing or other advantageous features as may be apparent to those reviewing this disclosure, the teachings disclosed herein extend to those embodiments which fall within the scope of the appended claims, regardless of whether they accomplish one or more of the above-mentioned advantages.

SUMMARY

A surgical cutting guide adapted to receive a cutting instrument during a surgical procedure is disclosed herein. In at least one embodiment, the surgical cutting guide comprises at least one body portion including a bone engaging surface. A plurality of separate plates are secured to the at least one body portion. At least one cutting slot is formed in the surgical cutting guide between the plurality of separate plates. The at least one cutting slot is configured to receive the cutting instrument and orient the cutting instrument for the surgical procedure.

In at least one embodiment, the surgical cutting guide comprises at least one body member comprised of a first material and at least one guide member comprised of a second material that is different than the first material. The first material may be, for example, a plastic material and the second material may be, for example, a metal material. The at least one guide member is positioned in the at least one body member such that the at least one guide member provides a wall of a cutting slot formed in the surgical cutting guide. Accordingly, the at least one body member comprises a seat adapted to receive the at least one guide member and properly orient the at least one guide member relative to the at least one body member.

The above described features and advantages, as well as others, will become more readily apparent to those of ordinary skill in the art by reference to the following detailed description and accompanying drawings.

DESCRIPTION

Figure 1:
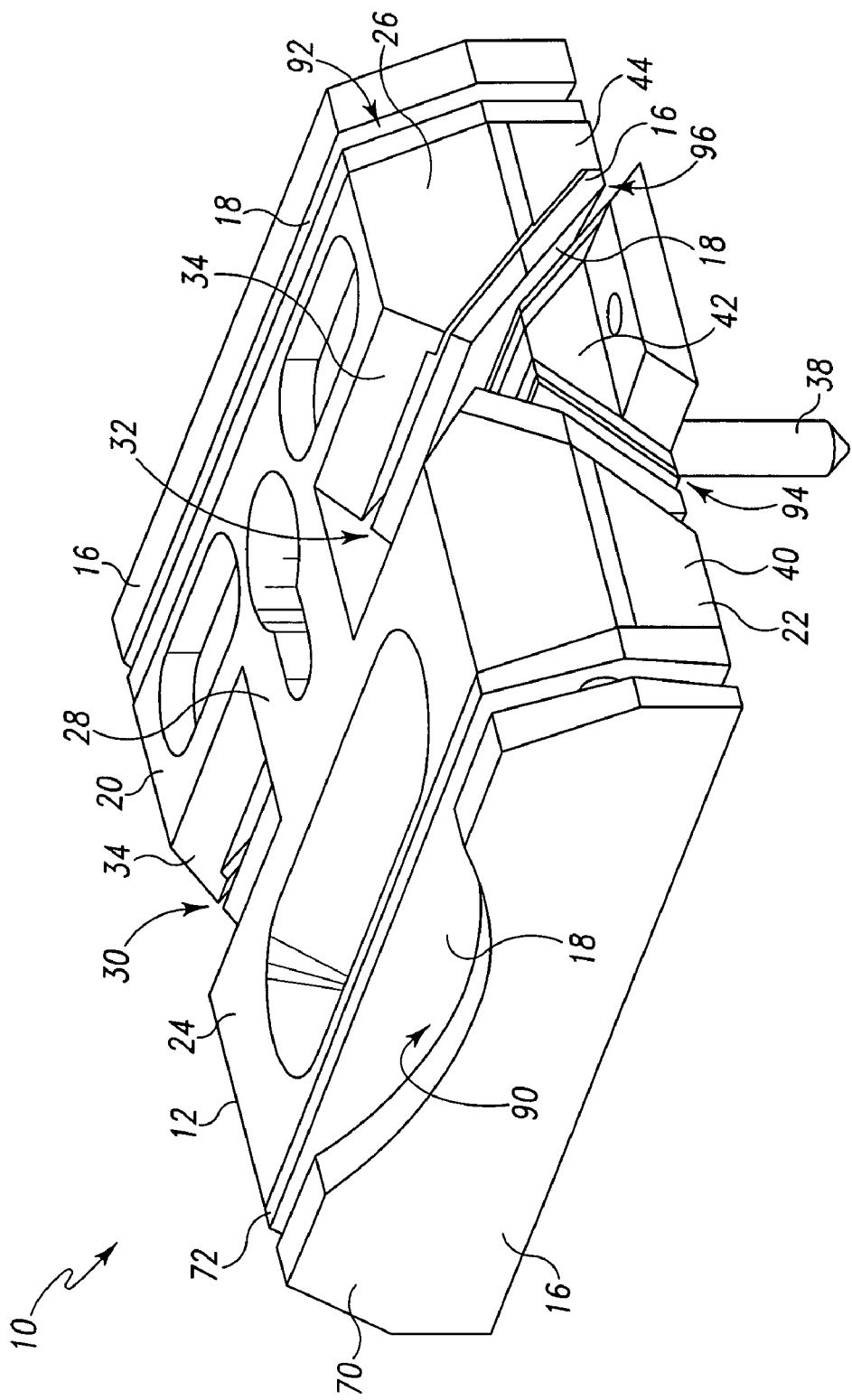
FIG. 1 shows a top perspective view of one embodiment of a surgical cutting guide.
Figure 2:
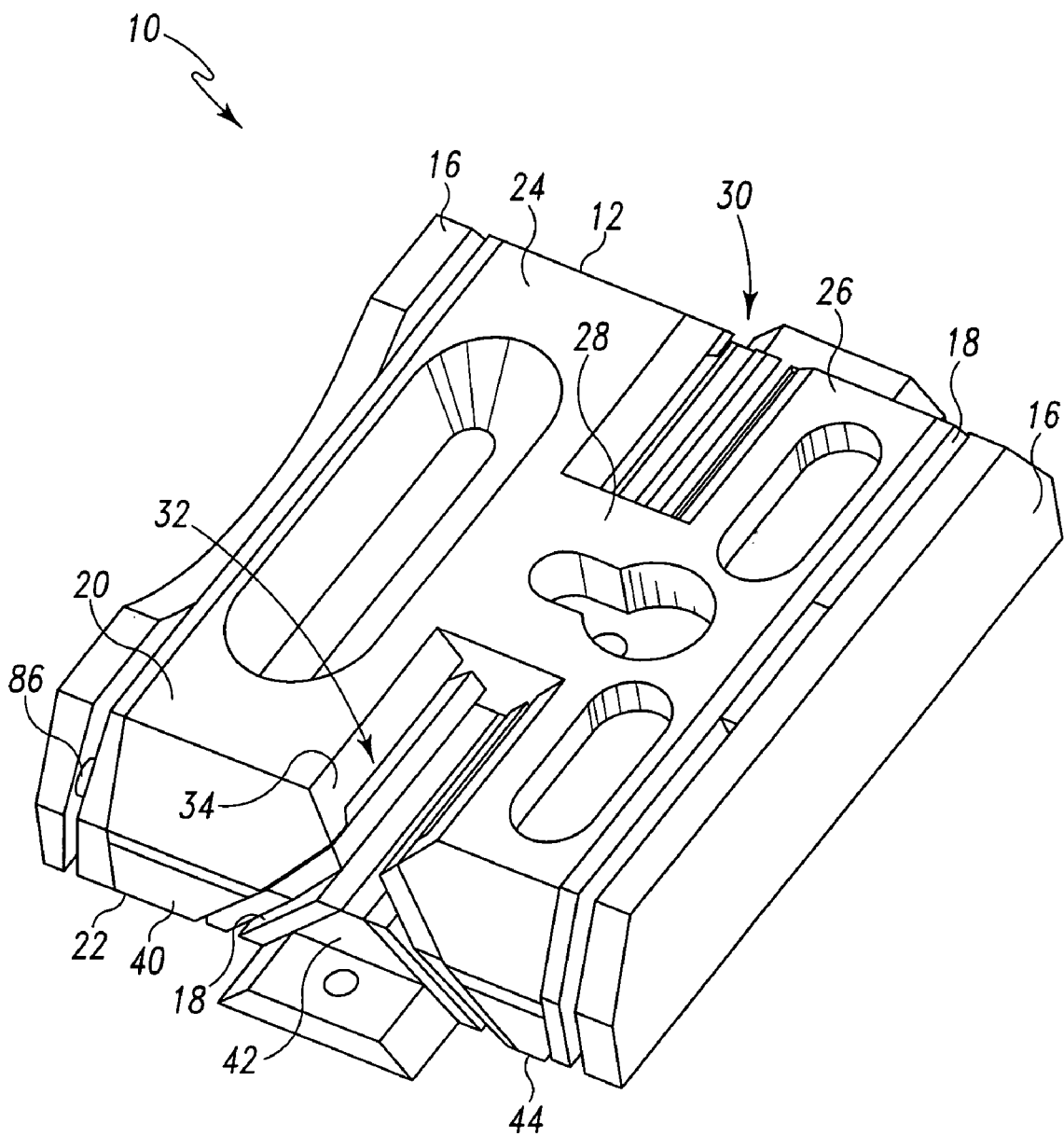
FIG. 2 shows another top perspective view of the surgical cutting guide of FIG. 1.

With general reference to FIGS. 1 and 2, one embodiment of a surgical cutting guide 10 is shown in the form of a distal cutting block for a femur. The surgical cutting guide 10 includes a block member 12 with a bone engaging surface 14. The surgical cutting guide 10 also includes a plurality of separate plates 16 positioned in the block member 12. A plurality of cutting slots 18 are formed in the surgical cutting guide 10. Each of the plurality of cutting slots 18 is provided between two opposing plates of the plurality of separate plates 16. The cutting slots 18 are designed and dimensioned to receive the blade of the cutting instrument and properly orient the blade in order to make a cut during the surgical procedure.

The block member 12 includes a superior body portion 20 and an inferior body portion 22. Both the superior body portion 20 and the inferior body portion 22 are comprised of a moldable plastic material, such as, for example, polyamide polyphenylsulfone, polyethersulfone, polysulfone, polyketone, or polyarylamide. It will be recognized that any of numerous other plastic materials could be used to form the superior body portion 20 and the inferior body portion 22.

The superior body portion 20 is provided as an H-shaped structure, including two side legs 24, 26, joined by a center cross-member 28. A number of openings are formed in superior body portion 20, including first central opening 30 and second central opening 32. Both the first opening 30 and the second opening 32 are designed to accept the blade of a saw used for a surgical procedure. These openings 30, 32 include chamfered sides 34 that allow the blade to enter the opening at an angle. As explained in further detail below, the openings 30, 32 provide entrances to the slots 18 formed in the block member 12 which orient the surgical blade to make a proper bone cut during the surgical procedure.

Figure 3:
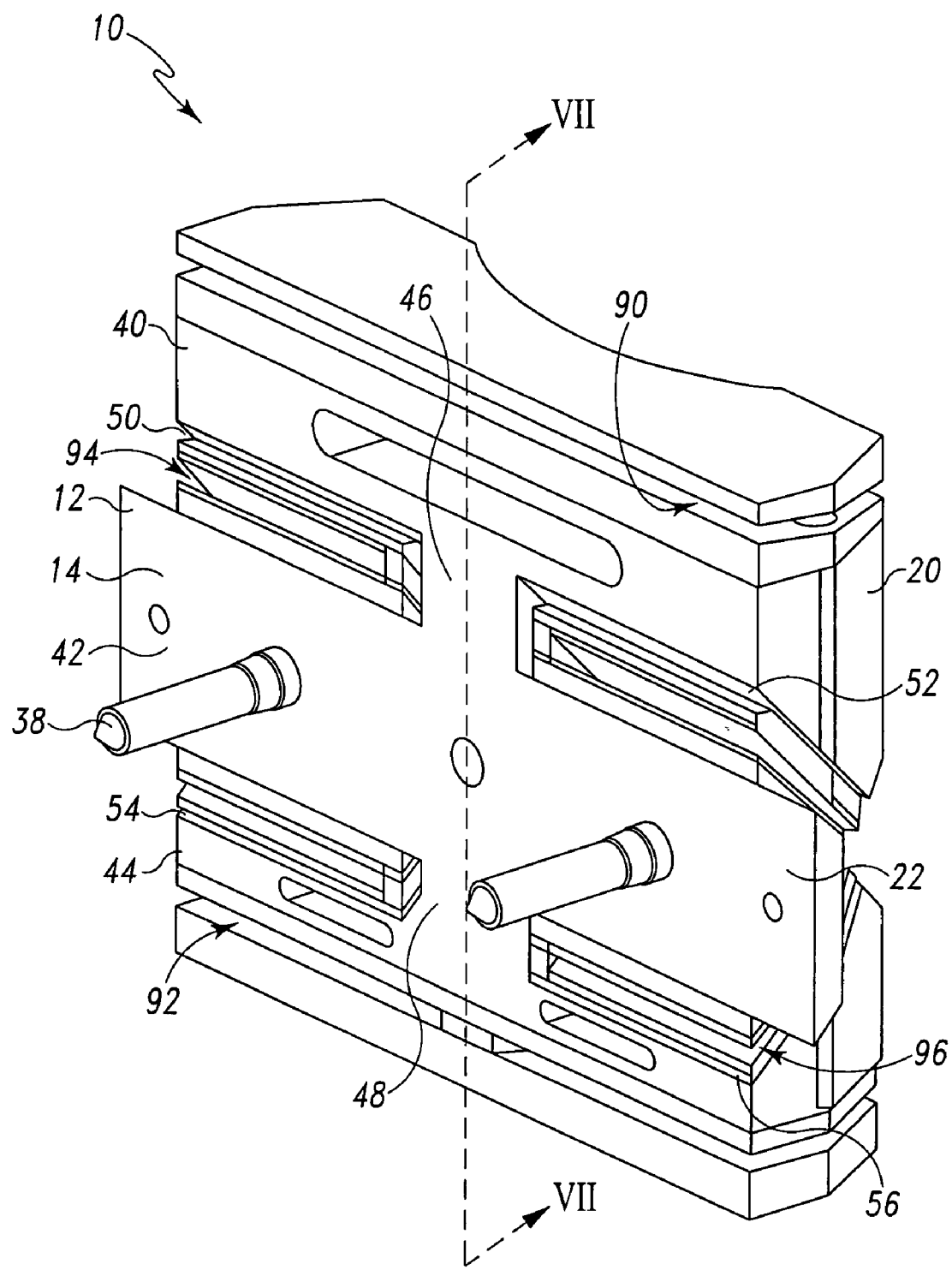
FIG. 3 shows a bottom perspective view of the surgical cutting guide of FIG. 1.

FIG. 3 shows a view of the inferior body portion 22 including the bone engaging surface 14 of the block member 12. The bone engaging surface 14 is the surface designed to engage the bone to be cut by the surgeon. The bone engaging surface 14 is a generally planar surface and includes two bone fasteners in the form of two pins 38 extending from the end. The pins 38 are configured to fit within holes drilled by the surgeon in the bone in order to hold the block member 12 in place during the surgery.

Figure 4:
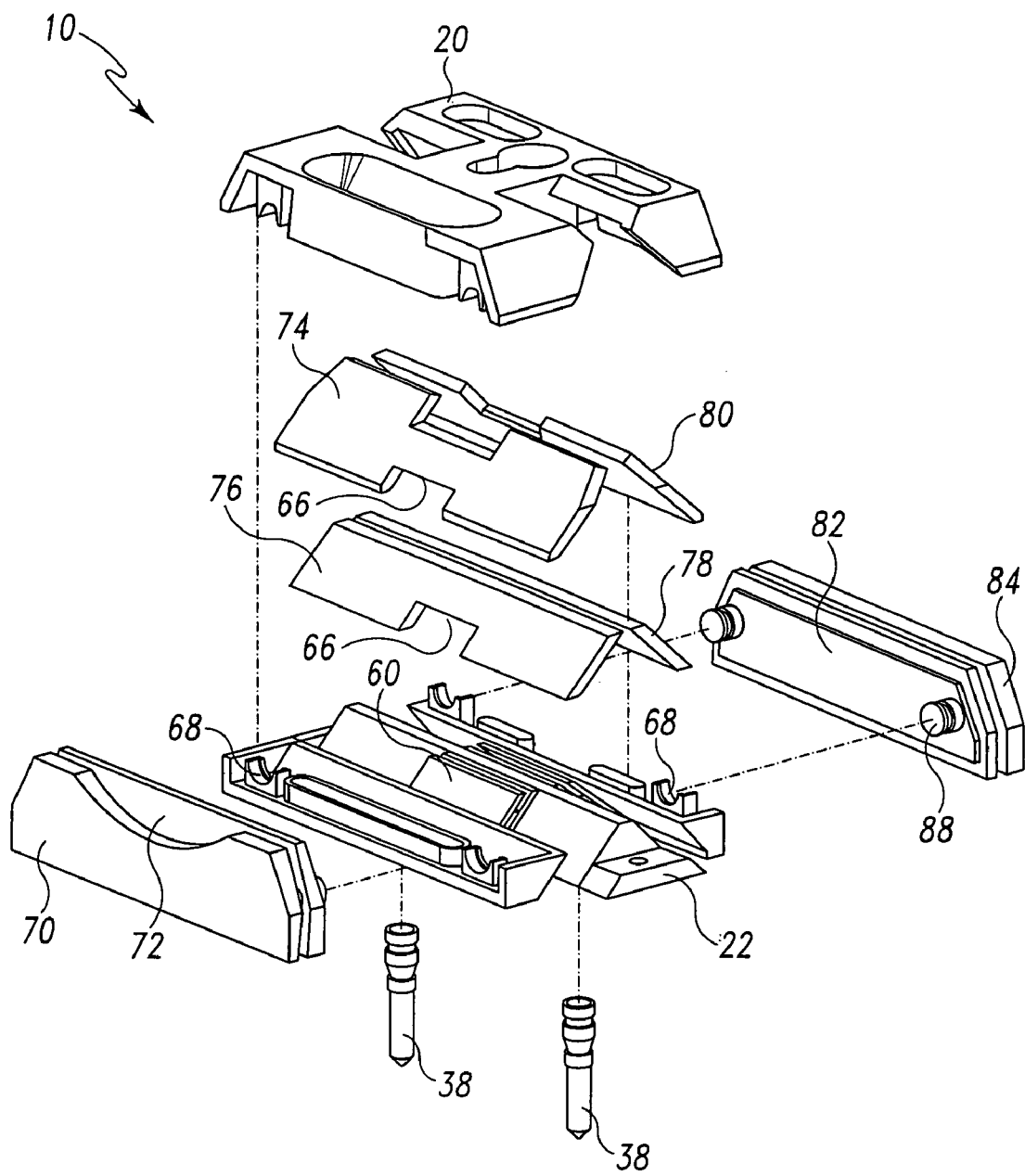
FIG. 4 shows an exploded assembly view of the surgical cutting guide of FIG. 1.

As best seen in FIGS. 3 and 4, the inferior body portion 22 is provided as a double-H type structure, including three legs 40, 42, and 44 joined by two center cross members 46, 48. The three legs include trapezoidal side legs 40 and 44 and triangular middle leg 42. The trapezoidal side legs 40, 44 each have a tapered side that is positioned opposite one of the tapered sides of the triangular leg 42. These opposing sides form slots 18 in the inferior body portion 22 of the block member 12.

The inferior body portion 22 also includes a number of openings, including openings 50, 52, 54 and 56. These openings 50, 52, 54, 56 provide exits from the slots 18 formed in the block member 12. Accordingly, when a surgical blade is inserted into one of the openings 30, 32 in the superior body portion 20, the blade passes through one of the slots 18 in the block member 12 and exits the block member 12 through one of the related openings 50, 52, 54, 56 in the inferior body portion 22.

Figure 7:
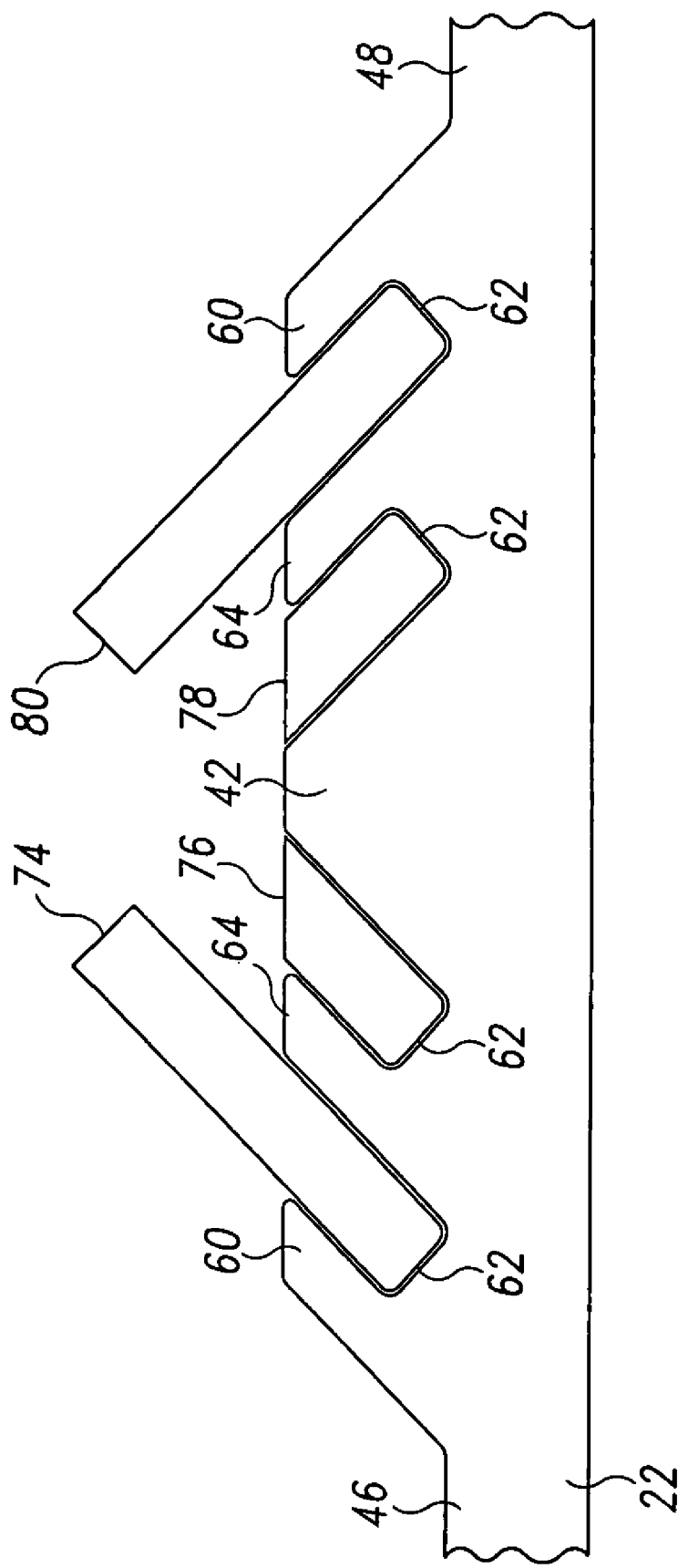
FIG. 7 shows a cross-sectional view of a plate seat in the surgical cutting guide of FIG. 1.

The inferior body portion 22 includes a number of seats 60, each seat 60 configured to hold one of the plates 16. As shown in FIG. 7, the seats 60 are provided by grooves 62 formed in the center cross members 46, 48 of the inferior body portion 22. The grooves 62 are designed and dimensioned to receive the plates 16 (and particularly plates 74, 76, 78 and 80) and retain the plates 16 in the block member 12. Two grooves 62 are provided on each side of the triangular leg 42. The two grooves 62 on each side of the triangular leg retain the plates in an angled position parallel to the tapered side of the triangular leg 42. In particular, the seats 60 retain the plates 16 such that the plates form an acute angle relative to the bone engaging surface 14 of the block member 12. The seats 60 also retain the plates in a spaced apart relationship directly opposite one another with a wedge 64 positioned between the plates. In particular, plate 74 is directly opposite plate 76 and plate 78 is directly opposite plate 80.

The plurality of plates 16 are comprised of a material that is different from the material of the block member 12. In one embodiment, the plurality of plates may be comprised of a metal material, such as a stainless steel material and/or a titanium material. It will be recognized that numerous other materials may also be used to form the plates 16. The plates 16 generally provide a durable, rigid material that resists wear when exposed to the back and forth motion of the surgeon's blade. Each plate is generally rectangular in shape with various features, such as seating features formed in its perimeter. Accordingly, the plates 16 may be formed from a large sheet of metal, by laser cutting, stamping, drilling, or otherwise cutting the sheet to produce the plates.

A total of eight plates 16 are provided on the block member 12. The plates 16 include two opposing first end plates 70, 72, two opposing first interior plates 74, 76, two opposing second interior plates 78, 80, and two opposing second end plates 82, 84.

As discussed above, the first opposing interior plates 74, 76 and second opposing interior plates 78, 80, are seated in the inferior body portion 22 at an acute angle relative to the bone engaging surface 14. To this end, the first opposing interior plates 74, 76 and second opposing interior plates 78, 80 include rectangular notches 66 that facilitate complete insertion of the plates into the seats 60. Thus, most of the perimeter of a notch 66 in a given plate 16 will fit into a groove 62 of a seat 60.

While the first opposing interior plates 74, 76, and second opposing interior plates 78, 80 are provided at an angle, the first opposing end plates 70, 72 and second opposing end plates 82, 84 are provided in an upright position, generally perpendicular relative to the bone engaging surface 14. The first opposing end plates 70, 72 and second opposing end plates 82, 84 are respectively separated by spacers 86 provided between the end plates 70, 72 and 82, 84. The end plates 70, 72 and 82, 84 may be welded, adhered, or otherwise fastened to the spacers 86. In one embodiment, the spacers 86 may be inserted into holes provided in the end plates 70, 72.

Figure 6:
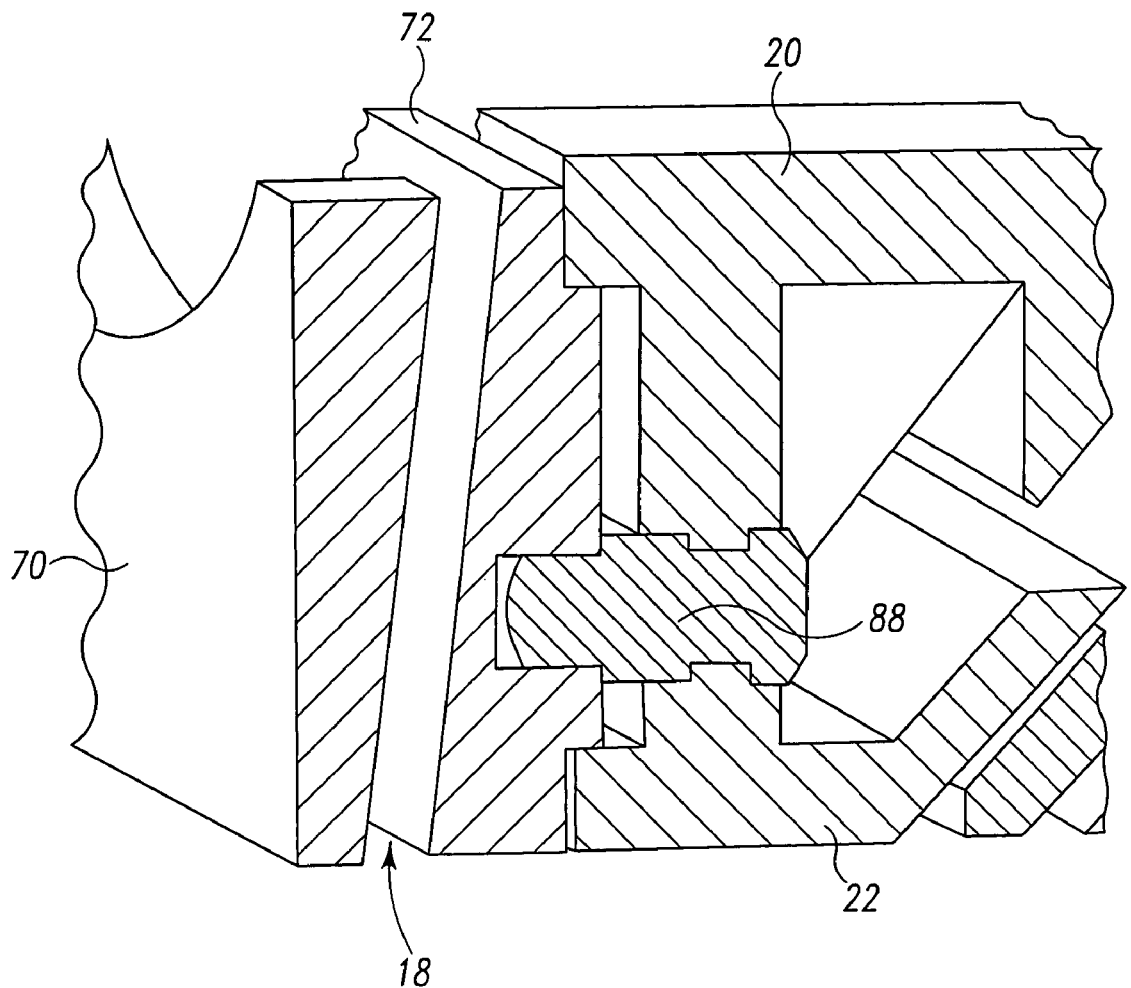
FIG. 6 shows a cross-sectional view of a fastening pin in the surgical cutting guide of FIG. 1.

Pins 88 may be used to secure the end plates 70, 72 and 82, 84 to the block member 12. For example, as shown in the embodiment of FIG. 6, a pin 88 is secured in a cavity formed in the inferior body portion 22. The opposite end of the pin 88 is configured to snugly fit into another cavity formed in the end plate 72. In this embodiment, the pins 88 may first be pressed into the cavities of the plates 70, 72, 82, 84, and then the opposite ends of the pins may be placed in bearings 68 in the inferior body portion 22 and trapped in the block member 12 when the superior body portion 20 is brought into engagement with the inferior body portion 22. Alternatively, the pins 88 may be molded into the block member 12 with the ends of the pins extending from the sides of the block member 12. In this embodiment, the plates 16 are then press-fit onto the sides of the block member 12 by forcing the ends of the pins 88 into the cavities in the end plates 70, 72, 82, and 84.

Figure 5:
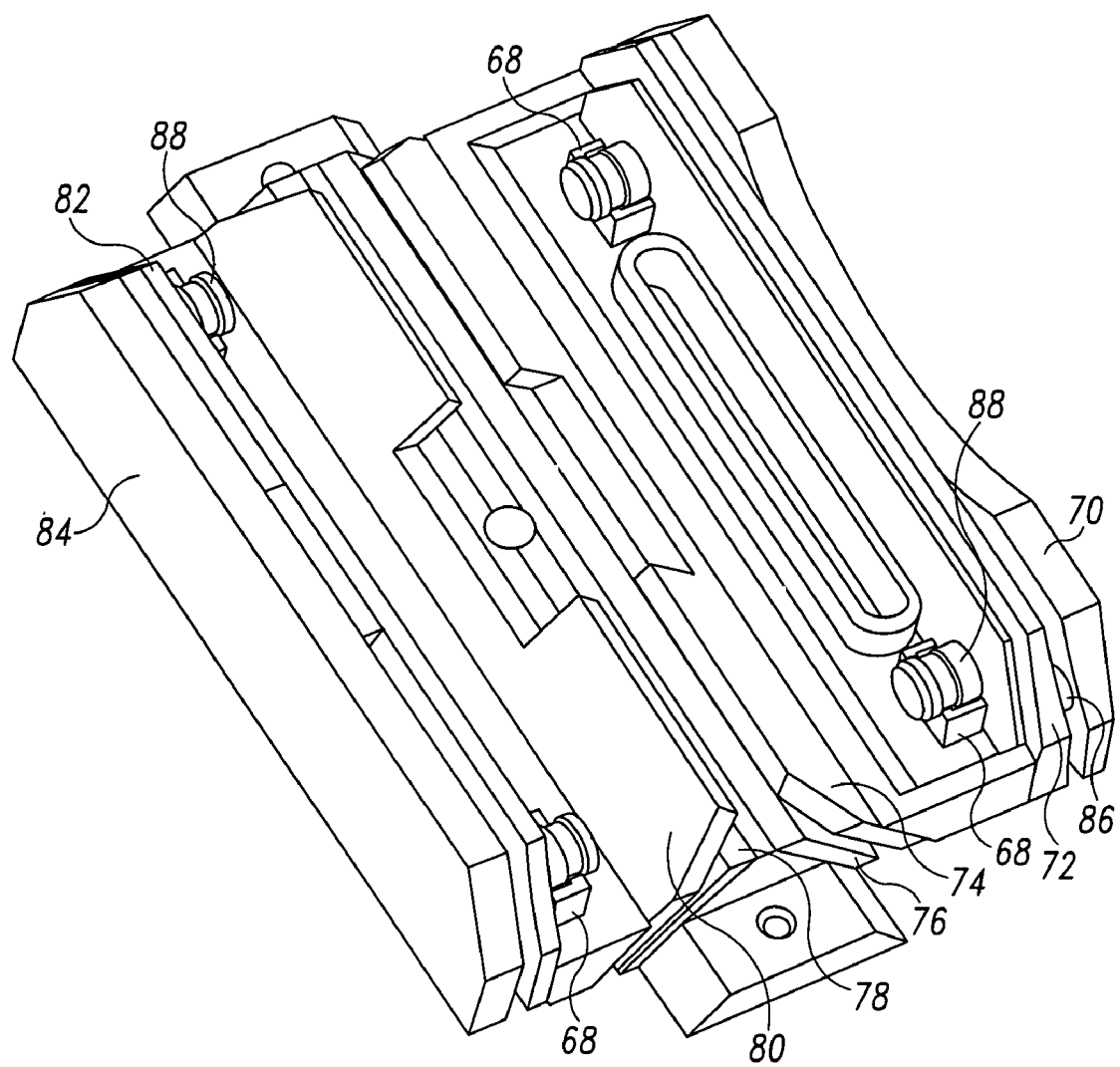
FIG. 5 shows a top perspective view of the surgical cutting guide of FIG. 1 without the superior body portion positioned on the cutting guide.

FIG. 4 shows an exploded assembly view of the surgical cutting guide 10. In order to assemble the surgical cutting guide 10, the interior plates 74, 76, 78 and 80 are positioned in the seats 60 of the inferior body portion 22. FIG. 5 shows a top perspective view of the interior plates 74, 76, 78, 80 following assembly of the plates into the seats 60 of the inferior body portion 22. As discussed previously, the seats 60 include grooves 62 configured to engage notches 66 formed in the plates 74, 76, 78, 80. FIG. 7 shows a cross-sectional view of the interior plates 74, 76, 78, 80 positioned in the seats 60 of the inferior body portion 22. A wedge 64 separates opposing plates 74, 76 and opposing plates 78, 80. Although not seen in the cross-sectional view of FIG. 7, cutting slots 18 are defined between the opposing plates 74, 76 and opposing plates 78, 80 to the sides of the cross-members 46, 48 (see cutting slots 94, 96 of FIG. 3).

Returning again to FIGS. 4 and 5, once the interior plates 74, 76, 78, 80 are positioned in the seats 60 of the inferior body portion 22, the end plates 70, 72, 82, 84 are positioned along the sides of the inferior body portion 22. As discussed previously, the end plates 70, 72, 82, 84 may be fastened to the sides of the inferior body portion 22 by placing the pins 88 secured to the end plates into the bearings 68 of the inferior body portion 22. After this, the superior body portion 20 is brought into place over the inferior body portion 22, and the superior body portion 20 is fastened to the inferior body portion 22. This fastening between the inferior 22 and superior body portions 20 may be accomplished by any of several means, including a screw or other fastener arrangement, a snap fit, ultra-sonic weld, adhesive, or any other means available to those of skill in the art. With the superior body portion 22 fastened to the inferior body portion 20, the plates 16 are locked in place on the block member 12.

Once the cutting guide 10 is assembled and the plates 16 are situated in the block member 12, opposing plates 16 in the block member define opposing walls of cutting slots 18 that extend through the block member. In particular the first opposing end plates 70, 72, define opposing walls for a first upright end slot 90. The second opposing end plates 82, 84 define opposing walls for a second upright end slot 92. The first opposing interior plates 74, 76 define opposing walls for a first angled slot 94. Finally, the second opposing interior plates 78, 80 define opposing walls for a second angled slot 96.

When using the cutting guide 10, the surgeon secures the cutting guide 10 to the bone, with the bone engaging surface 14 positioned next to the bone. For example, if the surgeon is performing a knee replacement, the surgeon would position the cutting guide 10 on the distal end of the femur. The cutting guide 10 may be held in place on the bone by the surgical team or the fastening pins 38 may be inserted into cavities drilled in the bone to secure the cutting guide in place. Once the cutting guide 10 is properly oriented and secured to the bone, the surgeon inserts the blade of a cutting instrument, such as the blade of a surgical saw, into one of the slots 90, 92, 94, 96 formed in the cutting guide 10. The slots 90, 92, 94, 96 allow the blade to pass completely through the cutting guide 10 and properly orient the blade for an ensuing cut by the surgeon. When the surgeon moves the blade back and forth during the cutting procedure, the plates 16 act as guide members in the slots 18, providing durable opposing slot walls that resist wear from the back and forth motion of the blade. Accordingly, with the cutting guide 10 properly positioned on the bone, the surgeon is provided with an effective tool for making proper cuts during the surgical procedure.

Although the present invention has been described with respect to certain preferred embodiments, it will be appreciated by those of skill in the art that other implementations and adaptations are possible. Moreover, there are advantages to individual advancements described herein that may be obtained without incorporating other aspects described above. Therefore, the spirit and scope of the appended claims should not be limited to the description of the preferred embodiments contained herein.

What is claimed is

1. A surgical cutting guide adapted to receive a cutting instrument during a surgical procedure, the surgical cutting guide comprising:
    at least one body portion including a bone engaging surface;
    a plurality of separate plates secured to the at least one body portion; and
    at least one cutting slot formed in the surgical cutting guide between the plurality of separate plates, the at least one cutting slot configured to receive the cutting instrument and orient the cutting instrument for the surgical procedure;
    wherein the at least one body portion includes a superior body portion and an inferior body portion with the plurality of separate plates trapped between the superior body portion and the inferior body portion;
    wherein the bone engaging surface is provided on the inferior body portion; and
    wherein at least one bone fastener extends from the bone engaging surface.

2. The surgical cutting guide of claim 1 wherein the plurality of separate plates include a first plurality of plates that form an angled cutting slot, the angled cutting slot forming an acute angle relative to a plane of the bone engaging surface.

3. The surgical cutting guide of claim 2 wherein the plurality of separate plates include a second plurality of plates that form a perpendicular cutting slot, the perpendicular cutting slot provided generally perpendicular to the plane of the bone engaging surface.

4. The surgical cutting guide of claim 1 wherein the plurality of separate plates include a first cutting plate and a second cutting plate, the first cutting plate including a notch that engages a slotted seat in the at least one body portion, wherein the slotted seat separates the first cutting plate from the second cutting plate.

5. The surgical cutting guide of claim 1 wherein the at least one body portion is comprised of a plastic material.

6. The surgical cutting guide of claim 5 wherein the plurality of separate plates are comprised of a metal material.

7. A surgical cutting guide comprising:
    at least one body member comprised of a plastic material, the at least one body member including a superior body portion and an inferior body portion; and
    at least one guide member comprised of a metal material, the at least one guide member positioned in a seat located between the superior body portion and the inferior body portion of the at least one body member such that the at least one guide member provides a wall of a cutting slot formed in the surgical cutting guide;
    wherein the inferior body portion includes a bone engaging surface, and
    wherein the at least one guide member comprises a plurality of separate plates secured to the at least one body member, the plates defining the cutting slot between them.

8. A surgical cutting guide adapted to receive a blade of a cutting instrument during a surgical procedure, the surgical cutting guide comprising:
    a block member including an inferior body portion having a bone engaging surface and a superior body portion connected to the inferior body portion;
    a plurality of guide members positioned in the cutting block, the plurality of guide members comprised of a different material than the block member; and
    at least one cutting slot extending through the block member, wherein the plurality of guide members define opposing walls of the at least one cutting slot, the at least one cutting slot adapted to receive the blade of the cutting instrument;
    wherein the plurality of guide members include a plurality of angled guide members defining opposing walls of an angled cutting slot that is generally at an acute angle with respect to the bone engaging surface; and
    wherein the plurality of guide members further comprise a plurality of upright guide members defining opposing walls of an upright cutting slot that is generally perpendicular to the bone engaging surface.

9. The surgical cutting guide of claim 8 wherein the plurality of guide members comprise a plurality of plates comprised of a metal material.

10. The surgical cutting guide of claim 8 wherein the plurality of plates are generally rectangular in shape and include seating features configured to engage seats for the plates provided in the cutting block.

11. The surgical cutting guide of claim 8 wherein the at least one of the plurality of guide members is fastened to the block member using a post member that extends from a cavity in the one of the plurality of guide members to a cavity in the block member.

* * * * *